(12) United States Patent
McPherson

(10) Patent No.: US 8,216,222 B2
(45) Date of Patent: **\*Jul. 10, 2012**

(54) TEMPERATURE SENSING RETURN ELECTRODE PAD

(75) Inventor: James W. McPherson, Boulder, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/085,973

(22) Filed: Apr. 13, 2011

(65) Prior Publication Data

US 2011/0190761 A1 Aug. 4, 2011

Related U.S. Application Data

(63) Continuation of application No. 11/529,007, filed on Sep. 28, 2006, now Pat. No. 7,927,329.

(51) Int. Cl.
*A61B 18/16* (2006.01)

(52) U.S. Cl. ............ 606/35; 606/32; 606/34; 607/152; 600/549

(58) Field of Classification Search ............. 606/32, 606/34–35; 607/152; 600/549
See application file for complete search history.

(56) References Cited

U.S. PATENT DOCUMENTS

| | | |
|---|---|---|
| 2,536,271 A | 1/1951 | Fransen et al. |
| 3,380,445 A | 4/1968 | Frasier |
| 3,534,306 A | 10/1970 | Watrous et al. |
| 3,543,760 A | 12/1970 | Bolduc |
| 3,642,008 A | 2/1972 | Bolduc |
| 3,683,923 A | 8/1972 | Anderson |
| 3,812,861 A | 5/1974 | Peters |
| 3,913,583 A | 10/1975 | Bross |
| 3,923,063 A | 12/1975 | Andrews et al. |
| 3,933,157 A | 1/1976 | Bjurwill et al. |
| 3,987,796 A | 10/1976 | Gonser |
| 4,067,342 A | 1/1978 | Burton |
| 4,092,985 A | 6/1978 | Kaufman |
| 4,094,320 A | 6/1978 | Newton et al. |
| 4,102,341 A | 7/1978 | Ikuno et al. |
| 4,114,622 A | 9/1978 | Gonser |
| 4,117,846 A | 10/1978 | Williams |
| 4,121,590 A | 10/1978 | Gonser |
| 4,126,137 A | 11/1978 | Archibald |
| 4,166,465 A | 9/1979 | Esty et al. |
| 4,188,927 A | 2/1980 | Harris |

(Continued)

FOREIGN PATENT DOCUMENTS

CA 1219642 3/1987

(Continued)

OTHER PUBLICATIONS

U.S. Appl. No. 10/609,946, filed Jun. 30, 2003, Jeffrey L. Eggleston.

(Continued)

*Primary Examiner* — Roy Gibson
*Assistant Examiner* — Kaitlyn Smith

(57) ABSTRACT

An electrosurgical return electrode is disclosed. The return electrode includes a conductive pad having one or more temperature monitoring zones and a patient-contacting surface configured to conduct electrosurgical energy and a temperature sensing circuit coupled to the conductive pad. The temperature sensing circuit includes at least one diode disposed within the at least one temperature monitoring zone, the at least one diode having a predetermined forward voltage drop that is indicative of temperature of at least one temperature monitoring zone.

20 Claims, 4 Drawing Sheets

U.S. PATENT DOCUMENTS

| | | | |
|---|---|---|---|
| 4,200,104 A | 4/1980 | Harris | |
| 4,200,105 A | 4/1980 | Gonser | |
| 4,213,463 A | 7/1980 | Osenkarski | |
| 4,231,372 A | 11/1980 | Newton | |
| 4,237,887 A | 12/1980 | Gonser | |
| 4,253,721 A | 3/1981 | Kaufman | |
| 4,303,073 A | 12/1981 | Archibald | |
| 4,304,235 A | 12/1981 | Kaufman | |
| 4,331,149 A | 5/1982 | Gonser | |
| 4,343,308 A | 8/1982 | Gross | |
| 4,381,789 A | 5/1983 | Naser et al. | |
| 4,384,582 A | 5/1983 | Watt | |
| 4,387,714 A | 6/1983 | Geddes et al. | |
| 4,393,584 A | 7/1983 | Bare et al. | |
| 4,416,276 A | 11/1983 | Newton et al. | |
| 4,416,277 A | 11/1983 | Newton et al. | |
| 4,437,464 A | 3/1984 | Crow | |
| 4,494,541 A | 1/1985 | Archibald | |
| 4,494,552 A * | 1/1985 | Heath | 600/509 |
| 4,643,193 A | 2/1987 | DeMarzo | |
| 4,657,015 A | 4/1987 | Irnich | |
| 4,658,819 A | 4/1987 | Harris et al. | |
| 4,662,369 A | 5/1987 | Ensslin | |
| 4,669,468 A | 6/1987 | Cartmell et al. | |
| 4,699,146 A | 10/1987 | Sieverding | |
| 4,722,761 A | 2/1988 | Cartmell et al. | |
| 4,725,713 A | 2/1988 | Lehrke | |
| 4,741,334 A | 5/1988 | Irnich | |
| 4,745,918 A | 5/1988 | Feucht | |
| 4,748,983 A | 6/1988 | Shigeta et al. | |
| 4,750,482 A | 6/1988 | Sieverding | |
| 4,754,757 A | 7/1988 | Feucht | |
| 4,768,514 A | 9/1988 | DeMarzo | |
| 4,770,173 A | 9/1988 | Feucht et al. | |
| 4,788,977 A | 12/1988 | Farin et al. | |
| 4,799,480 A | 1/1989 | Abraham et al. | |
| 4,807,621 A | 2/1989 | Hagen et al. | |
| 4,844,063 A | 7/1989 | Clark | |
| 4,848,335 A | 7/1989 | Manes | |
| 4,852,571 A | 8/1989 | Gadsby et al. | |
| 4,862,889 A | 9/1989 | Feucht | |
| 4,873,974 A | 10/1989 | Hagen et al. | |
| 4,878,493 A | 11/1989 | Pasternak et al. | |
| 4,887,047 A * | 12/1989 | Somerville | 330/257 |
| 4,895,169 A | 1/1990 | Heath | |
| 4,933,535 A * | 6/1990 | Zabinski | 219/497 |
| 4,942,313 A | 7/1990 | Kinzel | |
| 4,947,846 A | 8/1990 | Kitagawa et al. | |
| 4,955,381 A | 9/1990 | Way et al. | |
| 4,961,047 A | 10/1990 | Carder | |
| 4,969,885 A | 11/1990 | Farin | |
| 5,000,753 A | 3/1991 | Hagen et al. | |
| 5,004,425 A | 4/1991 | Hee | |
| 5,010,896 A | 4/1991 | Westbrook | |
| 5,038,796 A | 8/1991 | Axelgaard et al. | |
| 5,042,981 A | 8/1991 | Gross | |
| 5,061,914 A | 10/1991 | Busch et al. | |
| 5,087,257 A | 2/1992 | Farin et al. | |
| 5,114,424 A | 5/1992 | Hagen et al. | |
| 5,152,762 A | 10/1992 | McElhenney | |
| 5,160,334 A | 11/1992 | Billings et al. | |
| 5,196,008 A | 3/1993 | Kuenecke et al. | |
| 5,246,439 A | 9/1993 | Hebborn et al. | |
| 5,271,417 A | 12/1993 | Swanson et al. | |
| 5,276,079 A | 1/1994 | Duan et al. | |
| 5,286,255 A | 2/1994 | Weber | |
| 5,312,401 A | 5/1994 | Newton et al. | |
| 5,336,255 A | 8/1994 | Kanare et al. | |
| 5,352,315 A | 10/1994 | Carrier et al. | |
| 5,362,420 A | 11/1994 | Itoh et al. | |
| 5,370,645 A | 12/1994 | Klicek et al. | |
| 5,372,596 A | 12/1994 | Klicek et al. | |
| 5,385,679 A | 1/1995 | Uy et al. | |
| 5,388,490 A | 2/1995 | Buck | |
| 5,389,376 A | 2/1995 | Duan et al. | |
| 5,390,382 A | 2/1995 | Hannant et al. | |
| 5,409,966 A | 4/1995 | Duan et al. | |
| 5,447,513 A | 9/1995 | Davison et al. | |
| 5,449,365 A | 9/1995 | Green et al. | |
| 5,452,725 A | 9/1995 | Martenson | |
| 5,480,399 A | 1/1996 | Hebborn | |
| 5,496,312 A | 3/1996 | Klicek | |
| 5,496,363 A | 3/1996 | Burgio et al. | |
| 5,520,180 A | 5/1996 | Uy et al. | |
| 5,536,446 A | 7/1996 | Uy et al. | |
| 5,540,684 A | 7/1996 | Hassler, Jr. | |
| 5,585,756 A | 12/1996 | Wang | |
| 5,599,347 A | 2/1997 | Hart et al. | |
| 5,601,618 A | 2/1997 | James | |
| 5,611,709 A | 3/1997 | McAnulty | |
| 5,632,280 A | 5/1997 | Leyde et al. | |
| 5,633,578 A | 5/1997 | Eggers et al. | |
| 5,643,319 A | 7/1997 | Green et al. | |
| 5,660,892 A | 8/1997 | Robbins et al. | |
| 5,670,557 A | 9/1997 | Dietz et al. | |
| 5,674,561 A | 10/1997 | Dietz et al. | |
| 5,678,545 A | 10/1997 | Stratbucker | |
| 5,688,269 A | 11/1997 | Newton et al. | |
| 5,695,494 A | 12/1997 | Becker | |
| 5,707,369 A | 1/1998 | Vaitekunas et al. | |
| 5,718,719 A | 2/1998 | Clare et al. | |
| 5,720,744 A | 2/1998 | Eggleston et al. | |
| 5,766,165 A | 6/1998 | Gentelia et al. | |
| 5,779,632 A | 7/1998 | Dietz et al. | |
| 5,797,902 A | 8/1998 | Netherly | |
| 5,800,426 A | 9/1998 | Taki et al. | |
| 5,817,091 A | 10/1998 | Nardella et al. | |
| 5,830,212 A | 11/1998 | Cartmell et al. | |
| 5,836,942 A | 11/1998 | Netherly et al. | |
| 5,846,558 A | 12/1998 | Nielsen et al. | |
| 5,853,750 A | 12/1998 | Dietz et al. | |
| 5,868,742 A | 2/1999 | Manes et al. | |
| 5,924,983 A | 7/1999 | Takaki et al. | |
| 5,947,961 A | 9/1999 | Netherly | |
| 5,952,398 A | 9/1999 | Dietz et al. | |
| 5,971,981 A | 10/1999 | Hill et al. | |
| 5,976,128 A | 11/1999 | Schilling et al. | |
| 5,983,141 A * | 11/1999 | Sluijter et al. | 607/100 |
| 5,985,990 A | 11/1999 | Kantner et al. | |
| 5,999,061 A | 12/1999 | Pope et al. | |
| 6,007,532 A | 12/1999 | Netherly | |
| 6,010,054 A | 1/2000 | Johnson et al. | |
| 6,026,323 A * | 2/2000 | Skladnev et al. | 600/547 |
| 6,030,381 A | 2/2000 | Jones et al. | |
| 6,032,063 A | 2/2000 | Hoar et al. | |
| 6,039,732 A | 3/2000 | Ichikawa et al. | |
| 6,053,910 A | 4/2000 | Fleenor | |
| RE36,720 E | 5/2000 | Green et al. | |
| 6,059,778 A | 5/2000 | Sherman | |
| 6,063,075 A | 5/2000 | Mihori | |
| 6,083,221 A | 7/2000 | Fleenor et al. | |
| 6,086,249 A | 7/2000 | Urich | |
| 6,121,508 A | 9/2000 | Bischof et al. | |
| 6,135,953 A | 10/2000 | Carim | |
| 6,171,304 B1 | 1/2001 | Netherly et al. | |
| 6,200,314 B1 | 3/2001 | Sherman | |
| 6,203,541 B1 | 3/2001 | Keppel | |
| 6,214,000 B1 | 4/2001 | Fleenor et al. | |
| 6,232,366 B1 | 5/2001 | Wang et al. | |
| 6,240,323 B1 | 5/2001 | Calenzo, Sr. et al. | |
| 6,246,912 B1 * | 6/2001 | Sluijter et al. | 607/100 |
| 6,258,085 B1 | 7/2001 | Eggleston | |
| 6,258,087 B1 * | 7/2001 | Edwards et al. | 606/41 |
| 6,275,786 B1 | 8/2001 | Daners | |
| 6,283,987 B1 | 9/2001 | Laird et al. | |
| 6,301,500 B1 | 10/2001 | Van Herk et al. | |
| 6,310,611 B1 | 10/2001 | Caldwell | |
| 6,347,246 B1 | 2/2002 | Perrault et al. | |
| 6,350,264 B1 | 2/2002 | Hooven | |
| 6,350,276 B1 * | 2/2002 | Knowlton | 607/104 |
| 6,355,031 B1 * | 3/2002 | Edwards et al. | 606/31 |
| 6,356,779 B1 | 3/2002 | Katzenmaier et al. | |
| 6,357,089 B1 | 3/2002 | Koguchi et al. | |
| 6,358,245 B1 | 3/2002 | Edwards et al. | |
| 6,379,161 B1 | 4/2002 | Ma | |
| 6,409,722 B1 | 6/2002 | Hoey et al. | |
| 6,413,255 B1 | 7/2002 | Stern | |

| | | |
|---|---|---|
| 6,415,170 B1 | 7/2002 | Loutis et al. |
| 6,454,764 B1 | 9/2002 | Fleenor et al. |
| 6,488,678 B2 | 12/2002 | Sherman |
| 6,511,478 B1 * | 1/2003 | Burnside et al. ............... 606/41 |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 | 5/2003 | Eggleston |
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm et al. |
| 6,875,210 B2 | 4/2005 | Refior et al. |
| 6,892,086 B2 | 5/2005 | Russell |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,958,463 B1 | 10/2005 | Kochman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,112,201 B2 | 9/2006 | Truckai et al. |
| 7,128,253 B2 | 10/2006 | Mastri et al. |
| 7,137,980 B2 * | 11/2006 | Buysse et al. ............... 606/34 |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,452,358 B2 | 11/2008 | Stern et al. |
| 7,465,302 B2 | 12/2008 | Odell et al. |
| 7,473,145 B2 | 1/2009 | Ehr et al. |
| 7,483,738 B2 | 1/2009 | Tamarkin et al. |
| 7,520,877 B2 * | 4/2009 | Lee et al. ............... 606/42 |
| 7,566,332 B2 | 7/2009 | Jarrard et al. |
| 7,588,567 B2 | 9/2009 | Boveja et al. |
| 7,637,907 B2 | 12/2009 | Blaha |
| 7,722,412 B2 | 5/2010 | Ehr et al. |
| 7,722,603 B2 | 5/2010 | McPherson |
| 7,736,357 B2 | 6/2010 | Lee, Jr. et al. |
| 7,736,359 B2 | 6/2010 | McPherson |
| 7,771,419 B2 | 8/2010 | Carmel et al. |
| 7,771,422 B2 | 8/2010 | Auge, II et al. |
| 7,837,680 B2 | 11/2010 | Isaacson et al. |
| 7,909,819 B2 | 3/2011 | Falkenstein et al. |
| 7,927,329 B2 | 4/2011 | McPherson |
| 7,938,825 B2 | 5/2011 | Sturm et al. |
| 8,021,360 B2 | 9/2011 | Dunning et al. |
| 8,062,291 B2 | 11/2011 | McPherson |
| 8,080,007 B2 | 12/2011 | Dunning et al. |
| 8,100,898 B2 | 1/2012 | Gregg |
| 2003/0020072 A1 * | 1/2003 | Higgins ............... 257/78 |
| 2003/0120271 A1 * | 6/2003 | Burnside et al. ............... 606/41 |
| 2003/0139741 A1 | 7/2003 | Goble et al. |
| 2004/0150504 A1 | 8/2004 | Nicholson |
| 2004/0199154 A1 * | 10/2004 | Nahon et al. ............... 606/21 |
| 2004/0206365 A1 * | 10/2004 | Knowlton ............... 128/898 |
| 2005/0113817 A1 * | 5/2005 | Isaacson et al. ............... 606/32 |
| 2006/0041252 A1 | 2/2006 | Odell et al. |
| 2006/0074411 A1 * | 4/2006 | Carmel et al. ............... 606/32 |
| 2006/0079872 A1 * | 4/2006 | Eggleston ............... 606/35 |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 * | 3/2007 | Eggleston ............... 606/32 |
| 2007/0049919 A1 * | 3/2007 | Lee et al. ............... 606/34 |
| 2007/0074719 A1 | 4/2007 | Danek et al. |
| 2007/0161979 A1 * | 7/2007 | McPherson ............... 606/35 |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 * | 1/2008 | Ward ............... 606/32 |
| 2008/0082097 A1 * | 4/2008 | McPherson ............... 606/35 |
| 2008/0083806 A1 | 4/2008 | Scirica |
| 2008/0083813 A1 | 4/2008 | Zemlok et al. |
| 2008/0097558 A1 * | 4/2008 | Eggers et al. ............... 607/101 |
| 2008/0249524 A1 | 10/2008 | Dunning |
| 2008/0281310 A1 | 11/2008 | Dunning et al. |
| 2008/0281311 A1 * | 11/2008 | Dunning et al. ............... 606/32 |
| 2009/0036884 A1 | 2/2009 | Gregg et al. |
| 2009/0138006 A1 | 5/2009 | Bales et al. |
| 2009/0198229 A1 | 8/2009 | Dunning |
| 2009/0198230 A1 | 8/2009 | Behnke et al. |
| 2009/0209953 A1 | 8/2009 | Schoenman |
| 2009/0223041 A1 | 9/2009 | Garrison et al. |
| 2009/0234352 A1 | 9/2009 | Behnke et al. |
| 2009/0234353 A1 | 9/2009 | McPherson |
| 2010/0241023 A1 | 9/2010 | Gilbert |
| 2011/0077641 A1 | 3/2011 | Dunning |
| 2011/0112525 A1 | 5/2011 | Dunning et al. |
| 2011/0112530 A1 | 5/2011 | Keller |
| 2011/0190761 A1 | 8/2011 | McPherson |

FOREIGN PATENT DOCUMENTS

| | | |
|---|---|---|
| DE | 3239640 | 5/1983 |
| DE | 3206947 | 9/1983 |
| DE | 3544443 | 6/1987 |
| DE | 4238263 | 5/1993 |
| DE | 4231236 | 3/1994 |
| DE | 19717411 | 11/1998 |
| DE | 19751108 | 5/1999 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 1051949 | 11/2000 |
| EP | 1076350 | 2/2001 |
| EP | 0930048 | 4/2003 |
| EP | 1645236 | 4/2006 |
| EP | 1707151 | 10/2006 |
| EP | 1808144 | 7/2007 |
| EP | 1468653 | 11/2007 |
| EP | 1902684 | 3/2008 |
| EP | 1990020 | 11/2008 |
| EP | 1994905 | 11/2008 |
| EP | 2033588 | 3/2009 |
| FR | 2276027 | 6/1974 |
| FR | 2516782 | 5/1983 |
| GB | 2054382 | 2/1981 |
| GB | 2374532 | 10/2002 |
| WO | WO93/00862 | 1/1993 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/24092 | 3/2002 |
| WO | WO 02/058579 | 8/2002 |
| WO | WO 02/060526 | 8/2002 |
| WO | WO 02/099442 | 12/2002 |
| WO | WO 03/094766 | 11/2003 |

| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005/099606 | 10/2005 |
| WO | WO 2005/110263 | 11/2005 |
| WO | WO 2005/115262 | 12/2005 |
| WO | WO 2008/009385 | 1/2008 |
| WO | WO 2009/031995 | 3/2009 |
| WO | WO 2009/099960 | 8/2009 |

OTHER PUBLICATIONS

U.S. Appl. No. 11/900,190, filed Sep. 10, 2007, Jeffrey L. Eggleston.
U.S. Appl. No. 13/326,040, filed Dec. 14, 2011, Dunning et al.
U.S. Appl. No. 13/343,181, filed Jan. 4, 2012, William N. Gregg.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report—extended EP06008198.1 dated Jun. 18, 2010.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779—partial dated Sep. 8, 2008.
International Search Report EP08155779 dated Jan. 23, 2009.
International Search Report EP09003809.2 dated Jun. 29, 2009.
International Search Report EP09003813.4 dated Aug. 3, 2009.
International Search Report EP09152032 dated Jun. 17, 2009.
International Search Report EP09152130.2 dated Apr. 6, 2009.
International Search Report EP09152899.2 dated Jul. 1, 2009.
International Search Report EP10157054.7 dated Sep. 9, 2010.
International Search Report EP10190322.7 dated Feb. 18, 2011.
International Search Report PCT/US2004/004196 dated Oct. 4, 2007.

* cited by examiner

TEMPERATURE SENSING RETURN ELECTRODE PAD

CROSS-REFERENCE TO RELATED APPLICATION

This application is a continuation of U.S. application Ser. No. 11/529,007, filed Sep. 28, 2006, now U.S. Pat. No. 7,927,329, the entirety of which is hereby incorporated by reference herein for all purposes.

BACKGROUND

1. Technical Field

The present disclosure relates to electrosurgical apparatuses, systems and methods. More particularly, the present disclosure is directed to monopolar electrosurgical systems utilizing one or more return electrode pads configured to sense temperature.

2. Background of Related Art

Energy-based tissue treatment is well known in the art. Various types of energy (e.g., electrical, ultrasonic, microwave, cryo, heat, laser, etc.) may be applied to tissue to achieve a desired surgical result. Electrosurgery typically involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the user and applied to the tissue to be treated. The patient return electrodes are typically in the form of pads adhesively adhered to the patient and are placed remotely from the active electrode to carry the current back to the generator.

The return electrodes usually have a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heat applied to the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties (e.g., degree of electrode adhesiveness, temperature). These systems were only configured to measure temperature as a function of the changes in impedance of the return electrode pads.

SUMMARY

The present disclosure relates to an electrosurgical return electrode that includes a conductive pad having a patient-contacting surface. The conductive pad includes a temperature circuit coupled to a power source and electrically insulated from the patient-contacting surface. The temperature circuit includes one or more diodes coupled in series with one or more resistors. The diodes are located within predetermined temperature measuring zone and provide for temperature measurement within corresponding temperature monitoring zones. In particular, the forward bias voltage across the diodes varies with the temperature. Thus, by monitoring the voltage, temperature can be monitored as a function thereof.

According to one aspect of the present disclosure, an electrosurgical return electrode is provided. The return electrode includes a conductive pad having one or more temperature monitoring zones and a patient-contacting surface configured to conduct electrosurgical energy and a temperature sensing circuit operatively associated with the conductive pad. The temperature sensing circuit includes at least one diode disposed within the at least one temperature monitoring zone, the at least one diode having a predetermined forward voltage drop which is indicative of temperature of at least one temperature monitoring zone.

A method for performing electrosurgery is also contemplated by the present disclosure. The method includes the steps of providing an electrosurgical return electrode including a conductive pad having one or more temperature monitoring zones and a patient-contacting surface configured to conduct electrosurgical energy and a temperature sensing circuit operatively associated with the conductive pad. The temperature sensing circuit includes at least one diode disposed within the at least one temperature monitoring zone, the at least one diode having a predetermined forward voltage drop which is indicative of temperature of at least one temperature monitoring zone. The method also includes the steps of placing the electrosurgical return electrode in contact with a patient, generating electrosurgical energy via an electrosurgical generator, supplying the electrosurgical energy to the patient via an active electrode, and monitoring the predetermined forward voltage drop to measure the temperature of the at least one temperature monitoring zone.

According to another aspect of the present disclosure an electrosurgical system for performing electrosurgery is disclosed. The electrosurgical system includes an electrosurgical generator configured to provide electrosurgical energy and an electrosurgical return electrode. The return electrode includes a conductive pad having one or more temperature monitoring zones and a patient-contacting surface configured to conduct electrosurgical energy and a temperature sensing circuit operatively associated with the conductive pad. The temperature sensing circuit includes at least one diode disposed within the at least one temperature monitoring zone, the at least one diode having a predetermined forward voltage drop which is indicative of temperature of at least one temperature monitoring zone. The system also includes an active electrode to supply electrosurgical energy to a patient.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
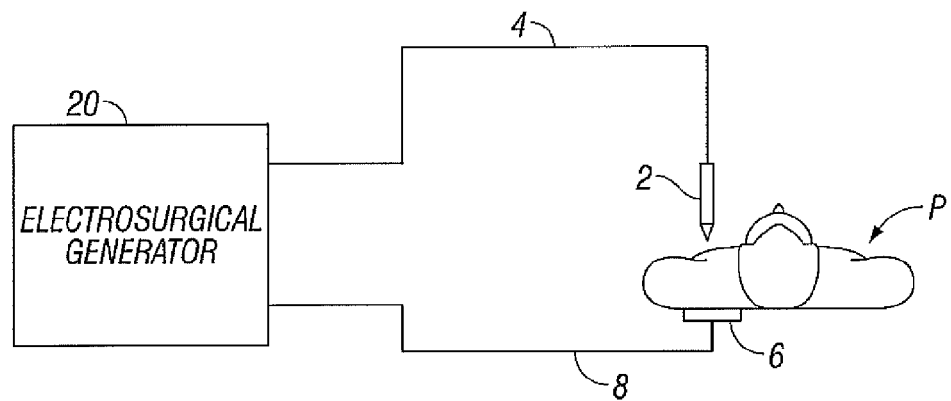
FIG. 1 is a schematic block diagram of an electrosurgical system according to the present disclosure.

FIG. 1 is a schematic illustration of an electrosurgical system according to one embodiment of the present disclosure. The system includes an electrosurgical instrument 2 having one or more electrodes for treating tissue of a patient P. The instrument 2 is a monopolar instrument including one or more active electrodes (e.g., electrosurgical cutting probe, ablation electrode(s), etc.). Electrosurgical RF energy is supplied to the instrument 2 by a generator 20 via an electrosurgical cable 4, which is connected to an active output terminal, allowing the instrument 2 to coagulate, seal, ablate and/or otherwise treat tissue. The energy is returned to the generator 20 through a return electrode 6 via a return cable 8. The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

The generator 20 includes input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
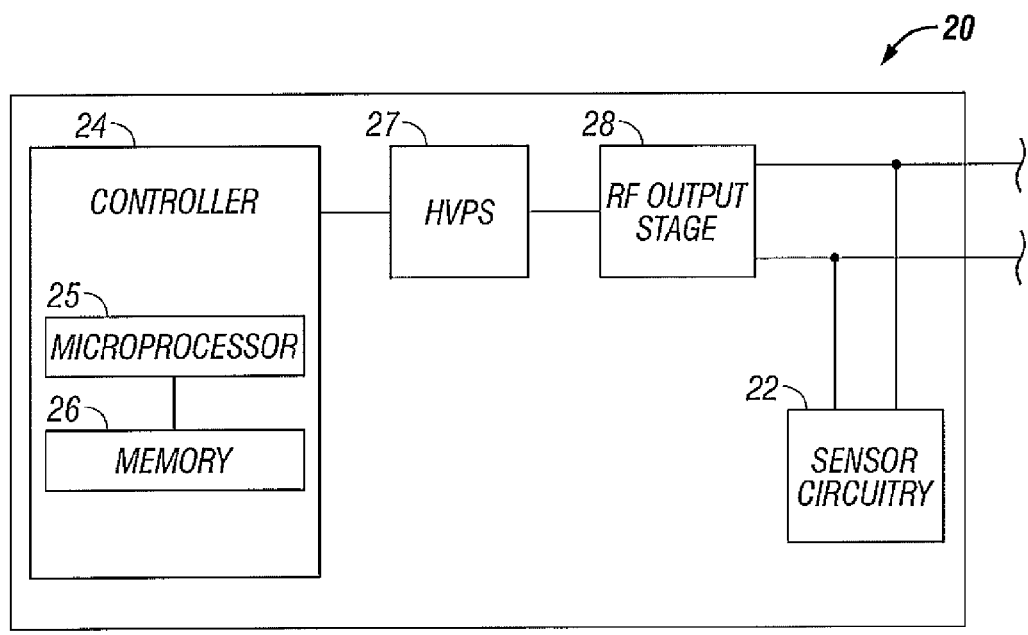
FIG. 2 is a schematic block diagram of a generator according to one embodiment of the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28, which then converts high voltage DC power into RF energy and delivers the RF energy to the active electrode. In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

Figure 3:
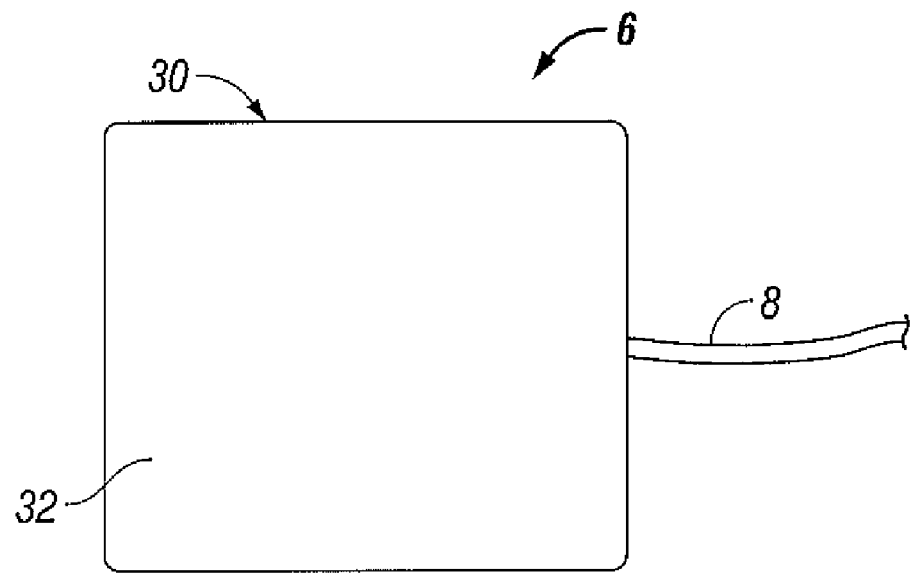
FIG. 3 is a top view of the electrosurgical return electrode of the monopolar electrosurgical system of FIG. 1.
Figure 4:
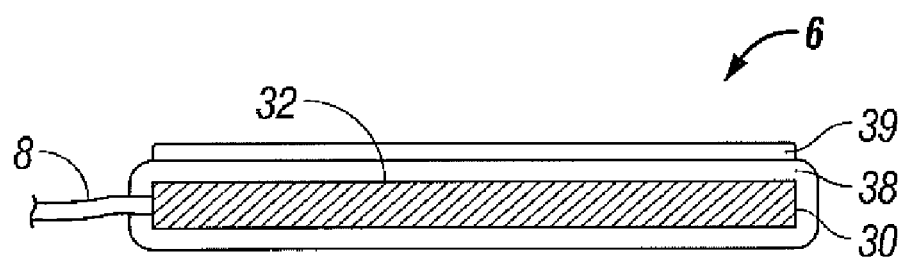
FIG. 4 is a cross-sectional side view of an electrosurgical return electrode having a positive temperature coefficient (PTC) material and adhesive material layers.

FIGS. 3 and 4 illustrate various embodiments of the return electrode 6 for use in monopolar electrosurgery. The return electrode 6 includes a conductive pad 30 having a top surface and a patient-contacting surface 32 configured to receive current during monopolar electrosurgery. The patient-contacting surface 32 is made from a suitable conductive material such as metallic foil. While FIG. 3 depicts the return electrode 6 in a general rectangular shape, it is within the scope of the disclosure for the return electrode 6 to have any suitable regular or irregular shape.

Referring to FIG. 4, another embodiment of the return electrode 6 is shown, wherein the conductive pad 30 includes a positive temperature coefficient (PTC) material layer 38 deposited thereon. The PTC material 38 can be made of, inter alia, a polymer/carbon-based material, a cermet-based material, a polymer material, a ceramic material, a dielectric material, or any combinations thereof. The PTC material layer 38 acts to distribute the temperature created by the current over the surface of the electrosurgical return electrode 6, which minimizes the risk of a patient burn. The return electrode 6 further includes an adhesive material layer 39 on the patient-contacting surface 32. The adhesive material can be, but is not limited to, a polyhesive adhesive, a Z-axis adhesive, a water-insoluble, hydrophilic, pressure-sensitive adhesive, or any combinations thereof, such as POLYHESIVE™ adhesive manufactured by Valleylab of Boulder, Colo. The adhesive material layer 39 ensures an optimal surface contact area between the electrosurgical return electrode 6 and the patient "P," which limits the possibility of a patient burn. In an embodiment where PTC material layer 38 is not utilized, the adhesive material layer 39 may be deposited directly onto the patient-contacting surface 32.

Figure 5A:
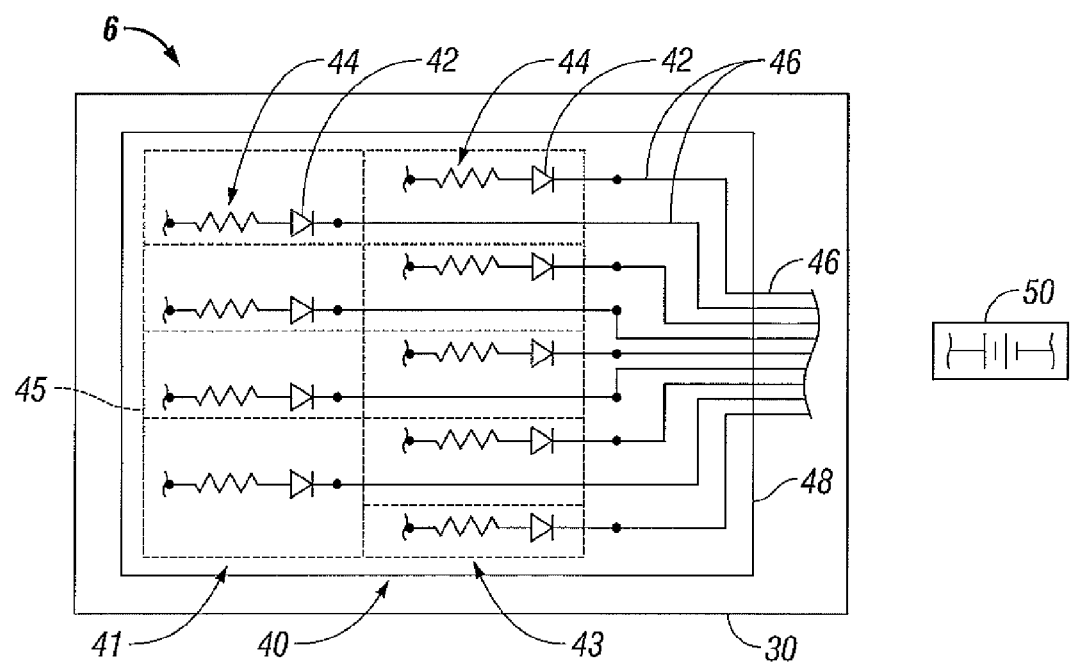
FIGS. 5A-B illustrate one embodiment of an electro surgical return electrode having temperature sensing circuit according to the present disclosure.
Figure 5B:
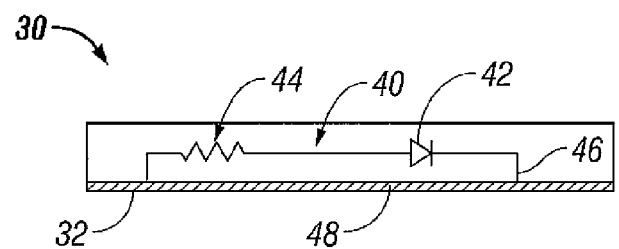

FIGS. 5A and 5B shows the return electrode 6 including a temperature sensing circuit 40 disposed therein. The temperature sensing circuit 40 includes one or more temperature sensor arrays 41 and 43 having at least one temperature sensor. Contemplated temperature sensors include thermocouples, thermistors, semiconductor (e.g., silicon) diodes, ferrite materials and Hall effect devices. The temperature sensing circuit 40 is disposed on a flex circuit (e.g., a flexible holding substrate 48) manufactured from suitable substrate, such as a polyimide film. Examples are films sold under the trademarks MYLAR™ and KAPTON™ and the like.

The diodes 42 are connected in series with one or more current limiting resistors 44 and are utilized as temperature sensors. The resistor 44 is coupled in series with the diode 42, having a resistance selected to set and limit the current flowing through the diode 42 at a predetermined level. The current flow to the diodes 42 is provided by a power source 50, such as a low voltage DC power source (e.g., battery, AC/DC transformer, etc.) connected in series with the diodes 42 and resistors 44 via interconnection wires 46. The power source 50 may be integrated into the generator 20 and draw power from the same source as the HVPS 27 (e.g., AC outlet). In one embodiment, interconnection of the diodes 42 and the resistors 44 is achieved by deposition of metal traces on the holding substrate 48 and soldering of the diodes 42 and the resistors 44 directly into the holding substrate 48. The holding substrate 48 may also electrically insulate the temperature sensing circuit 40 from the patient-contacting surface 32 to prevent RF energy being returned to the generator 20 from interfering with the circuit components.

The diodes 42 are forward biased such that current flows initially through the resistor 44 and from the diode's anode to the diode's cathode. In a forward biased diode 42, forward voltage drop (Vf) is produced that is in the range of about 0.5V to about 5V depending on the type of diode (e.g., light emitting diode). The forward voltage is directly dependent on the temperature. In particular, as the temperature increases, the semiconductor material within the diode 42 undergoes changes in their valence and conduction bands and consequently Vf decreases. Thus, by keeping the current flowing through the diode 42 constant via the resistor 44 and measuring the forward bias voltage allows for determination of the temperature of the diode 42.

The Vf signal is transmitted through the interconnection wires 46 to the generator 20, wherein the sensor circuit 22 analyzes the Vf to determine a corresponding temperature value. As those skilled in the art will appreciate, each of the interconnection wires 46 may include a corresponding isolation circuit (e.g., optical couplers) to translate electric signals (e.g., Vf) across isolation barriers, thereby isolating the temperature sensing circuit 40 from the RF supply.

The analysis process may include passing the Vf signals through an analog-to-digital converter and then multiplying the digitized Vf signal by a predetermined factor to arrive at a corresponding temperature value. The factor is derived empirically taking into consideration electrical properties of the diode 42, resistor 44 as well as electrical properties of the current being passed therethrough. The temperature signal is then transmitted to the controller 24 where it is further analyzed to determine appropriate action. For instance, comparing temperature measurements with a predetermined temperature threshold and adjusting or terminating the RF energy supply if the temperature measurement is larger than the predetermined threshold.

Temperature across the patient-contacting surface 32 may vary due to a number of factors (e.g., moisture content, adherence, etc.) affecting current density. Therefore, it may be desirable to measure temperatures at various points in the conductive pad 30. Measuring temperature at various points allows for pinpointing the location of so-called "hot spots," segments of the patient-contacting surface 32 where current density exceeds that of the surrounding area and results in pad burn. Since measurement of Vf for each diode 42 provides for determination of corresponding temperature at the location of the diode 42, placing the diodes 42 strategically within the conductive pad 30 allows for monitoring of temperature at those locations.

With reference to FIG. 5A, each resistor 44 and diode 42 pair is disposed within the conducting pad 30 such that the diode 42 provides temperature readings for a corresponding temperature monitoring zone 45. The size of the monitoring zone 45 depends on the distance between the diodes 42. The conductive pad 30 may include any number of monitoring zones 45 of varying sizes. Each diode 42 is identified by the sensor circuit 22 as being associated with a particular monitoring zone 45 such that, when Vf signals are transmitted and subsequently converted into temperature readings, the generator 20 provides temperature monitoring for each of the monitoring zones 45. This data is utilized to instruct the user which specific portion of the conductive pad 30 includes a hot spot so that preventative action may be taken, if necessary. This may include automatic RF supply termination and/or adjustment or manual termination of RF supply to ensure that the conductive pad 30 adheres properly to the patient at the identified hot spot.

Figure 6:
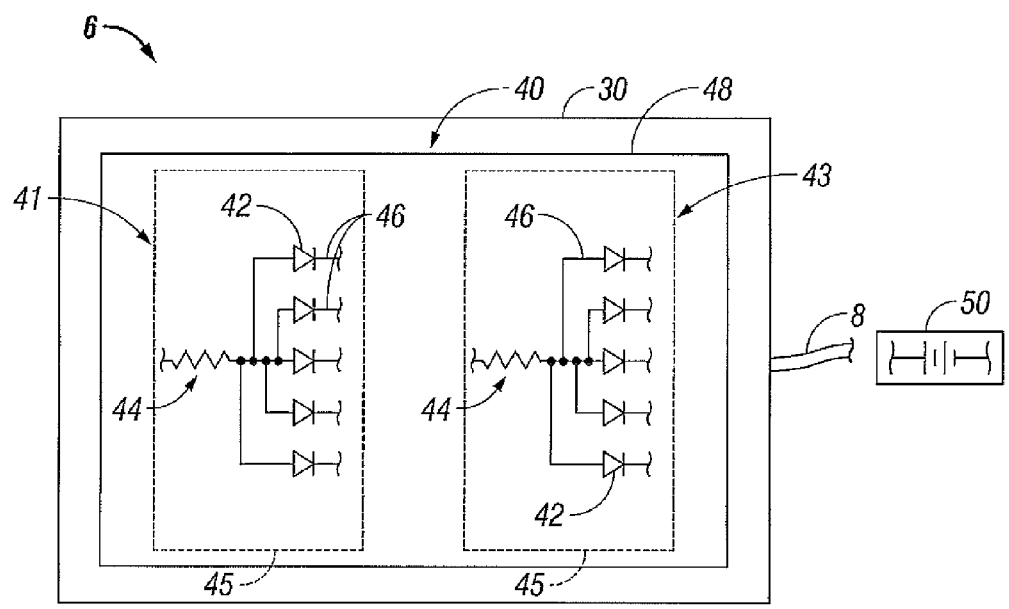
FIG. 6 is a cross-sectional plan view of another embodiment of an electrosurgical return electrode having temperature sensing circuit according to the present disclosure.

As shown in FIG. 6, the temperature sensor arrays 41 and 43 include a single resistor 44 connected in series with a plurality of diodes 42 disposed within a respective temperature monitoring zone 45. Since the diodes 42 are connected in series to one resistor 44, the current supplied to the diodes 42 is the same. Consequently, measuring the Vf across the diodes 42 provides the temperature for the entire respective temperature monitoring zone 45. This circuit arrangement provides an average temperature measurement over larger segments of the conductive pad 30 (e.g., entire area). Those skilled in the art will appreciate that various configurations of the resistor 44 and diode 42 are contemplated to ensure that temperature of various segments of the conductive pads 30 are monitored.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical return pad, comprising:
   a conductive electrode including a plurality of temperature monitoring zones contiguously arranged therein and a patient-contacting surface configured to conduct electrosurgical energy;
   a temperature sensing circuit thermally associated with each temperature monitoring zone configured to sense an average temperature of the temperature monitoring zone associated therewith; and
   an interconnection wire coupling each temperature sensing circuit to an optical isolation circuit adapted to isolate the temperature sensing circuit from electrosurgical energy.

2. An electrosurgical return pad according to claim 1, wherein the temperature sensing circuit includes one or more temperature sensing elements selected from the group consisting of a thermocouple, a thermistor, and a semiconductor diode.

3. An electrosurgical return pad according to claim 1, further comprising a holding substrate for housing the temperature sensing circuit, the holding substrate configured to electrically insulate the temperature sensing circuit from the patient-contacting surface.

4. An electrosurgical return pad according to claim 1, wherein the temperature sensing circuit is configured to operably couple to an electrosurgical generator.

5. The electrosurgical return pad according to claim 1, wherein the return pad includes an adhesive material disposed on the patient-contacting surface.

6. The electrosurgical return pad according to claim 1, wherein the return pad is at least partially coated with a positive temperature coefficient material.

7. A method for performing electrosurgery, comprising:
providing an electrosurgical return pad having a conductive electrode that includes a plurality of temperature monitoring zones contiguously arranged therein and a patient-contacting surface configured to conduct electrosurgical energy, a temperature sensing circuit thermally associated with each temperature monitoring zone and configured to sense an average temperature of the temperature monitoring zone associated therewith, and an interconnection wire coupling each temperature sensing circuit to an optical isolation circuit adapted to isolate the temperature sensing circuit from electrosurgical energy;
placing the electrosurgical return pad in contact with a patient;
generating electrosurgical energy from an electrical energy source;
supplying the electrosurgical energy to the patient via an active electrode; and
measuring the average temperature of the plurality of temperature monitoring zones.

8. A method according to claim 7, wherein the temperature sensing circuit includes one or more temperature sensing elements selected from the group consisting of a thermocouple, a thermistor, and a semiconductor diode.

9. A method according to claim 7, further comprising a holding substrate for housing the temperature circuit, the holding substrate configured to electrically insulate the temperature sensing circuit from the patient-contacting surface.

10. A method according to claim 7, wherein the return pad includes an adhesive material disposed on the patient-contacting surface.

11. A method according to claim 7, wherein the return pad is at least partially coated with a positive temperature coefficient material.

12. A method according to claim 7, further comprising:
identifying a segment of the patient-contacting surface corresponding to a temperature monitoring zone wherein current density exceeds that of the surrounding area; and
instructing a user to take action with respect to the identified segment.

13. An electrosurgical system for performing electrosurgery, the electrosurgical system comprising:
an electrosurgical generator configured to provide electrosurgical energy;
an electrosurgical return pad including a conductive electrode including a plurality of temperature monitoring zones contiguously arranged therein and a patient-contacting surface configured to conduct electrosurgical energy, and a temperature sensing circuit thermally associated with each temperature monitoring zone configured to sense an average temperature of the at least one temperature monitoring zone associated therewith, and an interconnection wire coupling each temperature sensing circuit to an optical isolation circuit adapted to isolate the temperature sensing circuit from electrosurgical energy; and
an active electrode configured to supply electrosurgical energy to a patient.

14. An electrosurgical system according to claim 13, wherein the temperature sensing circuit includes one or more temperature sensing elements selected from the group consisting of a thermocouple, a thermistor, and a semiconductor diode.

15. An electrosurgical system according to claim 13, further comprising a holding substrate for housing the temperature sensing circuit, the holding substrate configured to electrically insulate the temperature sensing circuit from the patient-contacting surface.

16. An electrosurgical system according to claim 13, wherein the return pad includes an adhesive material disposed on the patient-contacting surface.

17. An electrosurgical system according to claim 13, wherein the return pad is at least partially coated with a positive temperature coefficient material.

18. An electrosurgical system according to claim 13, further comprising:
an analog-to-digital converter unit configured to receive an analog temperature signal from a temperature sensing circuit of a temperature monitoring zone, and to output a corresponding digital temperature signal.

19. An electrosurgical system according to claim 18, further comprising:
a multiplication unit configured to multiply the digital temperature signal by a predetermined factor to arrive at a corresponding temperature value.

20. An electrosurgical system according to claim 19, wherein the electrosurgical generator terminates a supply of electrosurgical energy if the temperature value is larger than a predetermined threshold.

* * * * *